(12) United States Patent
Sene et al.

(10) Patent No.: US 6,344,194 B1
(45) Date of Patent: *Feb. 5, 2002

(54) METHOD FOR PREPARING A VIRAL AEROSOL AND ITS USE IN GENE THERAPY TREATMENT

(75) Inventors: Claude Sene, Mutzig; Didier Lamy, Strasbourg, both of (FR)

(73) Assignee: Transgene S.A., Strasbourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,930

(22) Filed: Jul. 21, 1999

Related U.S. Application Data

(62) Division of application No. 08/454,132, filed as application No. PCT/FR94/01245 on Oct. 26, 1994, now Pat. No. 5,952,220.

(30) Foreign Application Priority Data

Oct. 26, 1993 (FR) ............................................. 93 12743

(51) Int. Cl.$^7$ ......................... A61K 48/00; C12N 15/88
(52) U.S. Cl. .................. 424/93.2; 514/44; 435/320.1; 435/455; 435/456
(58) Field of Search .................... 514/44; 424/93.1, 424/93.2; 435/320.1, 455, 456

(56) References Cited

U.S. PATENT DOCUMENTS

| | | | |
|---|---|---|---|
| 4,039,656 A | * 8/1977 | Straub | 424/85 |
| 4,554,158 A | * 11/1985 | Russell | 424/89 |
| 4,649,911 A | * 3/1987 | Knight | 128/200.21 |
| 5,618,786 A | * 4/1997 | Roosdrorp et al. | 514/8 |
| 5,858,784 A | * 1/1999 | Debs et al. | 435/375 |
| 6,013,638 A | * 1/2000 | Crystal | 514/44 |

FOREIGN PATENT DOCUMENTS

| | | |
|---|---|---|
| FR | 2 423 2217 | 11/1979 |
| WO | WO 93/12240 | * 6/1993 |

OTHER PUBLICATIONS

Gunburg vol. 11. 9, pp. 414–417, 1995.*
Boucher, Tig, vol. 12, 3:81–84, 1996.*
Katkin et al., Human Gene Therapy, vol. 6, pp. 985–995, 1995.*
Stribling et al., PNAS, vol. 89, pp. 11277–11281, 1992.*
Wilson, Nature, vol. 365:691–692, 1993.*
Alton et al., Nature Genetics, vol. 5, pp. 135–142, 1993.*
Julie P. Katkin et al., "Aerosol Delivery of a β–Galactosidase Adenoviral Vector to the Lungs of Rodents", *Human Gene Therapy*, 6:985–995 (Aug. 1995), Mary Ann Liebert, Inc., Larchmont, New York, USA.
Wah Chiu et al. (Editors), "*Structural Biology of Viruses*", pp. 210–211, (1997), Oxford University Press, New York, USA.
Bluestone, *Bio/ Technology*, 10, 2:132–36 (1992).
U.S. Application Serial No. 07/769,623 (Crystal, Ronald G.), 1991.

* cited by examiner

Primary Examiner—Dave T. Nguyen
(74) Attorney, Agent, or Firm—Burns, Doane, Swecker & Mathis, L.L.P.

(57) ABSTRACT

A method of preparing a viral aerosol from a dilute viral suspension prepared by dissolving a virus in an aqueous solution containing 6–12 g/l of a monovalent cation salt, or 50–100 g/l of a hexose, which is then nebulised with a gas pressure of 0.5–3.5 bars or an ultrasonic frequency of 2–5 MHZ. The resulting aerosol composition is also disclosed.

11 Claims, No Drawings

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: human CFTR cDNA
      (C) INDIVIDUAL ISOLATE: [lacuna] synthetic oligonucleotide (vii) IMMEDIATE SOURCE:
      (B) CLONE: OTG3042

(xi) SEQUENCE DESCRIPTION: SEQ ID NO: 1:

GCAGTTGATG TGCTTGGCTA GAT                      23

(2) INFORMATION FOR SEQ ID NO: 2:

(i) SEQUENCE CHARACTERISTICS:
      (A) LENGTH: 21 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Adenovirus type 5
        (C) INDIVIDUAL ISOLATE: [lacuna] synthetic oligonucleotide (vii) IMMEDIATE SOURCE:
        (B) CLONE: OTG4347

(xi) SEQUENCE DESCRIPTION: SEQ ID NO: 2:

CAGCTCCTCG GTCACATCCA G                                         21

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: human CFTR cDNA
        (C) INDIVIDUAL ISOLATE: [lacuna] synthetic oligonucleotide (vii) IMMEDIATE SOURCE:
        (B) CLONE: OTG4905

(xi) SEQUENCE DESCRIPTION: SEQ ID NO: 3:

TGCTGCTCTC TAAAGCCTTG TATC                                      24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Adenovirus type 5
        (C) INDIVIDUAL ISOLATE: [lacuna] synthetic oligonucleotide (vii) IMMEDIATE SOURCE:
        (B) CLONE: OTG4908

(xi) SEQUENCE DESCRIPTION: SEQ ID NO: 4:

TCGTACCTCA GCACCTTCCA GATC                                      24

(2) INFORMATION FOR SEQ ID NO: 5:

(i) SEQUENCE CHARACTERISTICS:
        (A) LENGTH: 47 base pairs
        (B) TYPE: nucleic acid (C) STRANDEDNESS: single
            (D) TOPOLOGY: linear (ii) MOLECULE TYPE: cDNA to mRNA (iii) HYPOTHETICAL: NO (iv) ANTI-SENSE: YES (vi) ORIGINAL SOURCE:
            (C) INDIVIDUAL ISOLATE: [lacuna] synthetic oligonucleotide (vii) IMMEDIATE SOURCE:
            (B) CLONE: OTG5987

(xi) SEQUENCE DESCRIPTION: SEQ ID NO: 5:

CTTATACGGA TATCCTGGCA ATTCGGACTT ATTTGTGATG CTATTGC                47

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: human CFTR cDNA
            (C) INDIVIDUAL ISOLATE: [lacuna] synthetic oligonucleotide (vii) IMMEDIATE SOURCE:
            (B) CLONE: OTG5988

(xi) SEQUENCE DESCRIPTION: SEQ ID NO: 6:

AAGCAGTTGA TGTGCTTGGC TAGATCTGTT                                   30

(2) INFORMATION FOR SEQ ID NO: 7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (vi) ORIGINAL SOURCE:
            (C) INDIVIDUAL ISOLATE: [lacuna] synthetic oligonucleotide (vii) IMMEDIATE SOURCE:
            (B) CLONE: OTG5999

(xi) SEQUENCE DESCRIPTION: SEQ ID NO: 7:

CTTATACGGA TATCCTGGCA ATTCGGACTT                                   30

(2) INFORMATION FOR SEQ ID NO: 8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
        (ii) MOLECULE TYPE: DNA (genomic)

(iii) HYPOTHETICAL: NO (iv) ANTI-SENSE: YES (vi) ORIGINAL SOURCE:
             (A) ORGANISM: rhesus macaque polyoma virus (SV40)
             (C) INDIVIDUAL ISOLATE: [lacuna] synthetic oligonucleotide (vii) IMMEDIATE SOURCE:
             (B) CLONE: OTG4741

(xi) SEQUENCE DESCRIPTION: SEQ ID NO: 8:

GTAACCATTA TAAGCTGCAA TAAAC                                                   25
```

METHOD FOR PREPARING A VIRAL AEROSOL AND ITS USE IN GENE THERAPY TREATMENT

This application is a continuation, divisional, of application Ser. No. 08/454,132, filed June 8, 1995 now U.S. Pat. No. 5,952,220, which is the national phase application based on PCT/FR94101245, filed Oct. 26, 1994, which claims priority to French application 93 12743, filed Oct. 26, 1993.

The present invention relates to a method for preparing an aerosol comprising a virus.

Aerosol formulation of various substances, in particular medicinal substances, has been known for a very long time. Stability and negligible sedimentation rate constitute the essential features of an aerosol. For this reason, on the one hand, in order to prevent the particles aggregating with one another or displaying too high a sedimentation rate, properties incompatible with good efficiency, the proportions of constituents must satisfy a number of specific constraints due, in particular, to different environmental parameters such as the degree of humidity and the temperature, and on the other hand the formulation must take account of a number of difficulties mainly associated with the efficiency of the defence of the respiratory tract against aerial contaminants (clearance mechanisms), which tends to degrade inhaled active principles rapidly.

In particular, in the case where the active principle consists of viruses, the integrity of the viral particle is necessary for infection and penetration of the cells of the pulmonary epithelium, thereby imposing very specific conditions for obtaining the aerosol.

Generally speaking, during an aerolization, a virus may be inactivated as a result of three major causes. In the first place, loss of infectious power may result from the damage undergone by the virus during the nebulization process (spraying into the airways), it may also be inactivated in the aerosol by dehydration, and lastly it may be degraded in the potentially hostile environment represented by the mucus which coats the whole of the respiratory tract and which contains a large number of (proteolytic and other) enzymes.

It has now been demonstrated that viral inactivation can be limited and maintained within reasonable limits by applying, in order to obtain the aerosol, the method according to the invention employing particular conditions of nebulization and of packaging. In addition, this method enables the virus to be delivered effectively and in suitable amounts to the lung, in particular in the tracheobronchial passage.

Accordingly, the subject of the present invention is a method for obtaining a viral aerosol permitting, in particular, its administration via the airways of a mammal, characterized in that:

(a) a dilute viral suspension is prepared corresponding to the dilution of a viral suspension containing $10^4$ to $10^{13}$ plague forming units (pfu) of a virus in an aqueous solution containing at least 6 to 12 g/l of a salt of a monovalent cation or 50 to 100 g/l of a hexose; and (b) the dilute viral suspension is nebulized with a gas pressure of 0.5 to 3.5 bars or an ultra-sound frequency of 2 to 5 MHz.

The method according to the present invention is applicable to a very large number of viruses which can be administered by aerosol, in particular viruses chosen from the group consisting of poxviruses, retroviruses, herpesviruses, adeno-associated viruses, rhinoviruses, influenza viruses and adenoviruses.

In the context of the present invention, the term "virus" denotes both a natural virus as found in nature, and a modified virus whose genome contains modifications relative to that of the parent virus from which it originates. It can be an attenuated virus which has lost all or part of its pathogenic power relative to the natural virus from which it is derived. Its genome is modified in vivo in the course of successive passages in cell culture or in a living organism.

The term "virus" can also refer to a recombinant virus whose genome is modified in vitro by genetic engineering techniques. The modification can, for example, enable at least one gene essential to the viral replication to be inactivated (rendering the virus defective for replication), and/or a DNA fragment coding for a heterologous protein (normally not encoded by the natural virus) to be inserted. Insertion takes place in a suitable region of the viral genome, so as to permit the expression of the heterologous DNA fragment in a host cell. A host cell consists of any eukaryotic cell which can be infected by said virus, advantageously a human cell and preferably an epithelial cell of the tracheobronchial passage.

For the purposes of the present invention, the heterologous DNA fragment can originate from a eukaryotic organism or from a virus other than the one into which it is inserted. It may be isolated by any conventional technique in the field of the art, for example by cloning., PCR (Polymerase Chain Reaction) or chemical synthesis. It can be a fragment of genomic type DNA (containing all or part of the set of introns of the natural gene), of the complementary DNA type (cDNA; lacking introns) or of the minigene, that is to say mixed, type (containing at least all or part of an intron).

In accordance with the objectives pursued by the present invention, the heterologous DNA fragment may be placed under the control of the elements needed for its expression. "Elements needed" denotes the set of elements permitting transcription of said DNA fragment into messenger RNA (mRNA) or translation of the mRNA into protein.

The heterologous DNA fragment can code for (i) an intracellular protein, (ii) a membrane protein present at the surface of the host cell, or (iii) a protein secreted into the external medium. It can hence contain a signal sequence permitting secretion of the protein towards the membrane or out of the host cell.

Many recombinant viruses capable of benefitting from an administration by aerosol are described in the prior art. Their construction and propagation are within the capacity of a person skilled in the art. As examples, there may be mentioned Ad-α-1AT (Rosenfeld et al., 1991, Science, 252, 431–434), into the genome of which the human gene coding for al-antitrypsin (α1AT) is inserted, and Ad-CFTR (Rosenfeld et al., 1992, Cell, 68, 143–155), into the genome of which the human gene coding for the CFTR (for Cystic Fibrosis Transmembrane Conductance Regulator, in English) protein is inserted.

The method according to the present invention involves the preparation of a dilute viral suspension. This dilute viral suspension corresponds to the dilution of a viral suspension containing $10^4$ to $10^{13}$ pfu of virus in an aqueous solution containing at least 6 to 12 g/l of a salt of a monovalent cation or 50 to 100 g/l of a hexose.

In this step, the suspension to be diluted is generally composed of viruses placed in a buffered medium optionally containing a bivalent cation such as magnesium, calcium or manganese. This type of suspension also being usable for storage. For storage in frozen form, the suspension should be supplemented with a stabilizing agent such as glycerol at a concentration of at least 10%, or sucrose at a concentration of approximately 1 M.

The suspension of viral particles to be diluted can optionally comprise other substances, in particular human serum albumin (HSA), urea, sodium glutamate, glycine and inositol.

According to the method of the present invention, it is necessary for the viral suspension to comprise $10^4$ to $10^{13}$, advantageously $10^6$ to $10^{12}$ and preferably $10^8$ to $10^{11}$ pfu of a virus; the activity of this suspension will be able to depend, in particular, on the virus used.

This suspension to be diluted is then diluted with the aqueous solution according to a suspension/aqueous solution ratio by volume of 1:5 to 1:20, advantageously of 1:10 to 1:20, preferably of 1:12 to 1:18, and as an absolute preference approximately 1:16.

The aqueous solution preferably comprises 6 to 12 g/l of a salt of a monovalent cation, preferably a sodium salt or a potassium salt, and as an absolute preference potassium chloride, sodium lactate and/or sodium chloride. The concentration of salt of a monovalent cation is preferably 6 to 10 g/l, and as an absolute preference approximately 9 g/l.

When the aqueous solution comprises 50 to 100 g/l of a hexose, and preferably approximately 50 g/l, possible hexoses are, in particular, glucose and mannose.

In addition, the aqueous solution can comprise other compounds, such as a calcium salt, for example calcium chloride.

The suspension thus diluted enables an aerosol to be generated whose particular stability in the respiratory tract is sufficient to enable the virus to pass through it. Naturally, it is possible to obtain a corresponding viral suspension by another manipulation sequence.

The nebulization of the dilute suspension may be achieved by a gas pressure or by ultrasound. The conditions of this nebulization also constitute critical parameters of implementation of the method. According to a preferred embodiment of the method according to the present invention, the dilute suspension is subjected to a gas pressure of 0.5 to 3.5 bars, and as an absolute preference of 2 to 3.5 bars. Alternatively, it may also be subjected to an ultrasound frequency of 2 to 5 MHz, and preferably approximately 2 to 3 MHz. The gas pressure and also the ultrasound frequency may be applied by means of a nebulizer.

Generally speaking, a nebulizer is an apparatus permitting the administration of aerosols. The nebulizers may be of any type and their structures are known to a person skilled in the art, and these devices are commercially available.

When the method used entails the application of a gas pressure, a nebulizer of the pneumatic type, connected either to a source of compressed gas such as air or medical oxygen or to a pneumatic pump, is preferably employed. As regards the nebulizing of a dilute viral suspension with an ultrasound frequency, it is preferable to use an ultrasonic type nebulizer, which is provided with a quartz crystal vibrating at high frequency.

The method according to the invention is most especially well suited to the preparation of an aerosol intended for therapeutic purposes, to deliver an optimum amount of viral particles into the tracheobronchial passages of the respiratory tract.

Generally speaking, in man, the respiratory tract is composed of three distinct regions:
- the upper part which extends from the nose to the top of the trachea;
- The tracheobronchial passages which extend from the top of the trachea to the terminal bronchioles; and
- the alveolar region extending from the bronchioles to the alveolar sacs.

Among the diseases capable of being treated by employing the method according to the invention, lung diseases effecting the tracheobronchial passages may be mentioned, and in particular cystic fibrosis, pulmonary emphysema, asthma and lung cancer.

In this context, the viruses which it would be advantageous to deliver by carrying out the method according to the invention are preferably recombinant viruses whose genome comprises a DNA fragment coding for a heterologous protein capable, in particular, of inhibiting or slowing down the progression of a lung disease or preventing it becoming established. Among heterologous proteins, there may be mentioned those which are capable of:

- participating directly or indirectly in the transport of ions through cell membranes, and more specifically in the transport of chloride ($Cl^-$ or sodium ($Na^+$) ions, such as the CFTR protein (Riordan et al., Science, 245, 1066–1073);
- reducing the activity of the proteases present in the lungs, in particular in inflammatory conditions, such as native α1AT (Long et al., 1984, Biochemistry, 23, 4828–4837) or modified α1AT (Jallat et al., 1986, Protein Engineering, 1, 29–35); and
- inhibiting the growth of tumor cells by strengthening cellular immunity, such as interleukins (IL), interferons (IFN) or tumor necrosis factors (TNF), and by having a tunor-suppressive activity, such as the protein p53 (Baker et al., 1989, Science, 244, 217–221) or Rb (Friend et al., 1986, Nature, 323, 643646).

This list is not limiting. DNA fragments coding for other proteins described in the literature for their antitumor effect or their inhibitory effect with respect to the destruction of lung tissues may be used.

Lastly, the present invention also relates to a method of treatment of diseases of the airways, in particular of lung diseases in man, according to which an aerosol prepared according to the method according to which:

(a) a dilute viral suspension is prepared corresponding to the dilution of a viral suspension containing $10^4$ to $10^{13}$ pfu of virus in an aqueous solution containing at least 6 to 12 g/l of a salt of a monovalent cation or 50 to 100 g/l of a hexose;

(b) the dilute viral suspension is nebulized with a gas pressure of 0.5 to 3.5 bars or an ultrasound frequency of 2 to 5 MHz, is administered by inhalation, in the nasal or buccal cavity of a patient requiring such a treatment.

The inhalation can take place in a single dose or a dose repeated one or several times after a certain time interval.

The invention is described more completely by means of the following examples:

EXAMPLE 1

Preparation of an Aerosol from a Viral Suspension Stored in the Presence of 10% Glycerol and Diluted in a Solution of Monovalent Cation A viral suspension is prepared from a recombinant adenovirus into the genome of which the human gene coding for the CFTR protein (Ad-CFTR) is inserted, as described in Rosenfeld et al. (1992, supra).

Briefly, it is derived from adenovirus type 5, the genome of which lacks on the one hand the E1A gene coding for a trans-activating protein essential to the replication of the adenovirus, and on the other hand the nonessential E3 gene. The CFTR gene is inserted in place of the E1A gene.

Ad-CFTR is propagated by means of human embryonic kidney cell line 293 (Graham et al., 1977, J. Gen. Virol., 36, 59–72), which expresses the E1 function constitutively. This line is available at the ATCC (CRL 1573). The 293 cells are cultured according to the supplier's recommendations.

Cells in culture are infected before confluence with an initial inoculum of Ad-CFTR virus and according to a multiplicity of infection (moi) of 2 to 10. They are incubated at 37° C. and, as soon as cytopathic effects are observed, normally after 4 to 10 days of culture, the viruses are harvested according to the following protocol.

The cell suspension is centrifuged at low speed for 10 minutes. The cell pellet is resuspended in approximately 10 ml of GMEM medium (Glasgow Modified Eagle Medium, Gibco BRL, Cergy-Pontoise) supplemented with 2% of fetal calf serum. The viruses are separated from the cells by several successive freezing/thawing cycles in an ethanol-dry ice bath/water bath at 37° C. Following the last cycle, cell debris is removed by centrifugation at low speed for 5 to 10 minutes.

The viruses are purified from the centrifugation supernatant by fractionation on a cesium chloride gradient with two density layers, 1.40 and 1.25 g/ml, respectively. Centrifugation is carried out at 100,000 g for a few hours at room temperature. The viruses appear in the form of a white band located at the interface of the two layers, and are recovered using a syringe. They are subjected to EL second purification on a self-generated cesium chloride gradient prepared using a solution containing 1.33 g/ml. The viruses are likewise recovered by puncturing the tube with a syringe, and glycerol equivalent to $\frac{1}{10}$th of the volume is added.

The cesium chloride is removed by dialysis against a buffer containing 10 mM Tris-HCl, pH 7.4, 1 mM $MgCl_2$ and 10% glycerol.

The titer of the viral suspension thereby obtained is determined accurately according to the titration method in agar or at 30 h (Graham and Prevec, 1991, Methods in Molecular Biology, 7, 109–128, ed. E. J. Murray, The Human Press Inc. Clinton, N.J.). The suspension is distributed in tubes (Nunc or Nalgene) in 100 µl aliquots so as to contain $5\times10^9$ to $5\times10^{10}$ pfu each. These tubes, which constitute the stock viral suspension, are stored at −60° C. until used.

At the time of use, 1.5 ml of sodium chloride solution containing 9 g/l (Meram, Melun) are added to 100 µl of the Ad-CFTR suspension (at a concentration of $10^7$, $10^8$ or $10^9$ pfu). Controls performed show that the titer of the dilute viral suspension thereby obtained is stable for several hours at room temperature.

An accelerated stability study was also under-taken at 370° C. After dilution of the viral suspension to different concentrations ($10^9$, $10^7$, $10^5$ pfu/ml) in the above sodium chloride solution, a sample of each dilution is taken at regular intervals (t=0 h, 2 h, 4h and 24 h), and the viral infectivity is titrated by the agar or 30 h technique. Stability at 37° C. of the dilute viral suspension for more than 3 h is observed, especially at high concentration ($10^9$ and $10^7$ pfu/ml).

An aerosol is generated by placing the dilute viral suspension in the reservoir of an Optineb 709 nebulizer (Air Liquide, Paris). The latter is a pneumatic generating apparatus operating at high pressure and affording a choice of the carrier gas. It is connected to a source of compressed air, and a variable pressure of medical air may be applied. Aerosolization tests are performed in order to evaluate the optimum conditions to be applied to patients suffering from cystic fibrosis. In particular, the effect of pressure (from 1 to 3.5 bars) and of the respiratory rate are studied. The latter defines a number of breaths per minute, and may be predetermined by setting the apparatus. In this connection, setting to position 7 corresponds to the respiratory rate of a child, while position 9 corresponds to that of an adult.

Aerosolization is carried out in 3 steps (viral suspension diluted, followed by two rinses of the cup with the sodium chloride diluent solution). The Optineb is set to self-triggering and connected to a trap or collector, for example a collectron MD8 (Sartorius, Palaiseau, FRANCE), to the end of which is fitted a gelatin filtering membrane enabling the viral particles to be recovered after nebulization. This membrane is then dissolved at 37° C. in 10 mM Tris-HCl buffer, pH 7.4, 1 mM $MgCl_2$ and 10% glycerol, and the infectivity of the viruses recovered is titrated by the 30 h and agar technique. This measurement enables the amount of active virus capable of entering a patient's airways to be evaluated. Under the different test conditions and relatively repeatedly, the trapped infectious viruses represent 15 to 40% of the initial number of viruses. Although some fluctuations are observed, best recovery yields are obtained at high pressure (3.5 bars), this being the case in both setting positions. As a guide, the recovery yield of medicinal products applied by aerosolization is usually approximately 10%. These results make it possible to envisage the use of the aerosolization of Ad-CFTR recombinant adenoviruses for the treatment of patients suffering from cystic fibrosis.

EXAMPLE 2

Preparation of an Aerosol from a Viral Suspension Stored in the Presence of 1M Sucrose and Diluted in a Solution of Monovalent Cation Example 1 is repeated with the following variant:

After recovery of the viruses after the second cesium chloride gradient, the viruses are dialyzed against 10 mM Tris-HCl buffer, pH 7.4, 1 mM $MgCl_2$ and 1M sucrose.

Aerosolization tests are performed as described in Example 1, at a pressure of 3.5 bars and a setting of the Optineb at position 9. A recovery yield of active viral particles of 27% is obtained.

EXAMPLE 3

Preparation of an Aerosol from a Viral Suspension Diluted in a Glucose Solution

Example 1 is repeated with the following variant:

A dilute viral suspension is prepared by adding 100 µl of the viral suspension to 1.5 ml of a glucose 10 solution containing 50 gl (Laboratoire Chaix du Marais Lavoisier, Paris).

When the dilute viral suspension is subjected to an accelerated stability study at 37° C., under the same conditions as those defined in Example 1 except that dilution is performed in the glucose solution, it is observed that the viral activity is stable for more than 2 hours.

EXAMPLE 4

Preparation of an Aerosol by Ultrasonic Vibration

Example 1 is repeated with the following variant:

An aerosol is generated employing an SAM LS ultrasonic nebulizer (System Assistance Medical, Le Léedat, France), used according to the supplier's recommendations. The dilute viral suspension obtained according to Example 1 is introduced into the cup of the nebulizer, and subjected to an ultrasonic vibration produced by a quartz crystal vibrating at a frequency of 2.4 MHz. Under these conditions, the recovery yield is of the order of 10%.

EXAMPLE 5

Preclinical Trials in Primates

The objective of these trials is to establish that aerosolization of recombinant adenoviruses permits in vivo transfer of the CIPTR gene into lung cells, and to evaluate the toxicity of the treatment.

A. Procedure

The experiment includes 5 rhesus monkeys (Macaca mulatta) (TNO Center for Animal Research, Rijswijk, Holland). The animals selected are in good health and weigh 5 to 10 kg. They were divided into three groups:

Group 1 consists of 2 monkeys to which a single dose of Ad-CFTR is administered (at D=0), a high dose ($7.5 \times 10^9$ pfu) for the first monkey and a low dose ($1.5 \times 10^7$ pfu) for the second. They are sacrificed at D+10.

Group 2 also consists of 2 monkeys which receive two administrations at an interval of 10 days (D=0 and D+10) of equivalent doses of Ad-CFTR ($7.5 \times 10^9$ pfu and $1.5 \times 10^7$ pfu, respectively). They are sacrificed at D+13.

The control group comprises one monkey treated with a control fluid (10 mM Tris-HCl pH 7.4, 1 mM $MgCl_2$ and 10% glycerol) according to the protocol applied to group 2 (2 successive administrations at D=0 and D+10 before being sacrificed at D+13).

100 gl of the Ad-CFTR solution adjusted to the concentrations stated above (group [sic] 1 and 2), or 100 µl of control solution (group 3), are added to 1.5 ml of a sodium chloride diluent solution containing 9 g/l, and placed in the cup of an Optineb apparatus. Nebulization is carried out on the anesthetized monkeys via a tube introduced into the trachea and connected to the nebulizer. Operating conditions are as follows: setting at position 7, medical air pressure 3.5 bars and nebulization in two steps (administration of the dilute viral solution followed by rinsing with 800 µl of diluent solution).

B. Analysis of the Dissemination Power of the Viruses

The stools of each of the animals are collected regularly and cultured on permissive 293 or HepG2 cells in order to test for the presence of recombinant or wild-type viral particles, respectively. After approximately 3 and 7 days of culture, such particles are detected by indirect immunofluorescence using a specific monoclonal antibody, for example an antibody recognizing the adenovirus 5 capsid protein (Bio-Science 012070). These analyses proved negative in all the monkeys in the experiment, indicating that the risk of dissemination of the virus in the environment is low or even zero.

C. Analysis of the Transfer of the CFTR Gene in Vivo

The methodology employed is described in Bout et al. (1994, Hum. Gene Therapy, 5, 3–10). Briefly, the main organs (liver, testicles, and the like), as well as tissue samples distributed over the entire length of the airways, are removed from the sacrificed animals. When the DNA has been extracted, adenoviral sequences are tested for by PCR, using primers specific for Ad-CFTR located at the junction of the CFTR expression cassette and the adenoviral vector, respectively OTG3042 (SEQ ID NO: 1, hybridizing with the CFTR sequence) and OTG4347 (SEQ ID NO: 2, recognizing the adenovirus type 5 sequence). At the end of 30 amplification cycles, the PCR products are separated by agarose gel electrophoresis and transferred onto a Hybond N+ membrane (Amersham), before being hybridized with a specific probe (SEQ ID NO: 3) labelled with $^{32}P$ by phosphorylation. A specific signal is obtained only in the trachea and the lungs of the monkeys in group [sic] 1 and 2 treated with a high viral dose ($7.5 \times 10^9$ pfu). It is of interest to note that all the other organs tested are negative.

It is necessary to increase the sensitivity of the technique in order to detect the presence of adenoviral sequences in the monkeys which have received the viral dose of $1.5 \times 10^7$ pfu. To this end, after 30 initial cycles of PCR, a further 30 cycles are performed employing OTG3042 and an internal primer OTG4908 (SEQ ID NO: 4). The PCR products are then treated as described above. A signal is obtained in about half of the samples removed from the airways. Hence it seems that the administration of the viruses by aerosol in the lungs is dose-dependent. Naturally, the hybridization is negative for the control monkey.

On the whole, these results indicate that Ad-CFTR remains contained within the target organ, namely the airways.

D. In Vivo Expression of the CFTR Gene

Expression of the human CFTR gene is studied in the samples removed from the airways by the technique of reverse transcription of RNA followed by a PCR (Shouldiner et al., 1993, in Methods in Molecular Biology, 15, 169–176, ed: white [sic], Human Press Inc, Totowa, N.J.). This technique, which has the advantage of being highly specific, will enable the presence of mRNA coding for human CFTR to be visualized. The RNA is isolated from the samples by conventional techniques. 1 µg of total RNA is reverse transcribed in the presence of MoMLV (Moloney Murine Leukemia Virus) reverse transcriptase using a primer possessing at its 5' end a unique identification sequence (termed tag in English). More precisely, the primer (OTG5987; SEQ ID NO: 5) comprises 30 nucleotides of identification sequence and 17 nucleotides corresponding to the polyadenylation signal and permitting reassociation with the CFTR mRNAs originating from the transcription of Ad-CFTR. PCR is then carried out directly on the above reaction mixture employing the primers OTG5988 (SEQ ID NO: 6) and OTG5999 (SEQ ID NO: 7 corresponding to the identification sequence of OTG5987) for the first 30 amplification cycles, and then OTG5988 and OTG4741 (SEQ ID NO: 8) for a further 30 cycles. The amplification products are analyzed as described above.

Human CFTR mRNAs are detected in the samples of pulmonary lobes of the monkeys to which one or two viral doses of $7.5 \times 10^9$ pfu has/have been administered. In contrast, no signal is detected in samples originating from the control monkey, or from the monkeys which have received the low viral dose.

These results show that the nebulization of appropriate doses of Ad-CFTR results in an expression of the functional CFTR gene in lung cells, and are especially encouraging with a view to the treatment of cystic fibrosis by gene therapy.

E. Pathology

Generally speaking, the nebulization of Ad-CFTR is not associated with a weight loss or an abnormal behavior of the monkeys, or with significant disturbances of the hematological and biochemical serum parameters.

In order to evaluate the pulmonary functions more precisely, post-mortem histopathological analyses are performed on sections of tissues removed from different parts of the airways, according to the methodology described in Bout et al., (1994, supra). These sections are examined with a view to looking for signs of inflammation and lesions of the pulmonary epithelium. The results are as follows. In all the monkeys, pulmonary architecture is intact. Minor inflammatory manifestations and squamous metaplasia are observed, unconnected with the administration of Ad-CFTR since they are also present in the control monkey.

However, additional lesions of low intensity (perivascular and peribronchial lymphocytic infiltrations and interstitial pneumonia) were noted in the 2 monkeys which received a high viral dose, without any significant difference being apparent between the animals in group I [sic] (nebulization of a dose of $7.5 \times 10^9$ pfu) and those in group II [sic] (nebulization of two doses of $7.5 \times 10^9$ pfu).

In conclusion, the administration of Ad-CFTR by aerosol is well tolerated by all the animals treated. These studies enabled it to be checked that the Ad-CFTR recombinant virus remains contained in the lung and does not disseminate in the body. Although pulmonary lesions are observed following the administration of high viral doses, these do not appear to lead to serious pathologies. These preclinical trials enable it to be concluded that treatment in man is feasible.

EXAMPLE 6

Method of Treatment of Cystic Fibrosis

Example 1 is repeated with the following variants:

An aerosol is generated by placing the dilute viral suspension of Example 1 in the reservoir of the Optineb 709, the latter being set to the appropriate position (7 or 9) in accordance with the patient's respiratory rate. After 100 $\mu$l have been sampled for the purpose of subsequent analyses, the apparatus is connected to a source of medical air. The buccal nozzle of the apparatus is placed in the mouth of a patient suffering from cystic fibrosis, and a gas pressure of 3.5 bars is applied (first nebulization).

Nebulization of the aerosol in the airways is triggered by the patient's inspiration. Nebulization ceases before the beginning of the expiratory phase; thereby enabling loss of material and discharge of the aerosol into the environment to be avoided.

The doses of aerosol delivered at each inspiration are adjusted in accordance with the patient's respiratory capacities. For an infant, who has a respiratory rate of 30 to 40 cycles/minute, the average amount administered per puff should be 1.8 $\mu$l. For a child with a respiratory rate of 20 to 25 cycles/minute, a dose of 3.2 $\mu$l is administered in each puff. Lastly, for an adult, who has a respiratory rate of 15 to 20 cycles/minute on average, a volume of 5 $\mu$l of the aerosol is administered in each puff.

According to these criteria, 160 puffs of the aerosol are delivered to an adult, enabling a volume corresponding to about half of the initial dilute viral solution to be nebulized.

Shortly after this first series of inhalations, 900 $\mu$l of the sodium chloride solution containing 9 g/l are added into the reservoir of the nebulizer. As before, a gas pressure of 3.5 bars is applied and a second series of inhalations also comprising 160 puffs is performed. Lastly, a third series is performed under the same conditions, after 900 $\mu$l of the sodium chloride solution containing 9 g/l have been introduced into the reservoir of the apparatus.

What is claimed is:

1. An aerosol obtained by a method comprising:

a) preparing a dilute viral suspension corresponding to the dilution of a viral suspension containing $10^4$ to $10^{13}$ pfu of recombinant adenovirus particles in an aqueous solution, wherein the dilute viral suspension limits inactivation of the virus and wherein said dilution is performed according to a viral suspension/aqueous solution ratio by volume of 1:5 to 1:20 and wherein said aqueous solution contains at least 6 to 12 g/l of a salt or a monovalent cation of 50 to 100 g/l of a hexose: and b) nebulizing the dilute viral suspension under conditions sufficient to produce a viral aerosol composition.

2. A method for delivering an optimum amount of viral particles into the tracheobronchial passages of the respiratory tract of a mammal comprising administering the aerosol of claim 1.

3. A method of increasing the transport of Cl⁻ ions in a lung of a mammal suffering from cystic fibrosis, comprising administering to said mammal in need of increase Cl⁻ transport, a therapeutically effective amount of the viral aerosol of claim 1 wherein said adenoviral particles are replication-defective adenoviral particles encoding a functional CFTR protein, and wherein a sufficient quantity of said CFTR protein is produced to increase Cl⁻ secretion in the lung.

4. The aerosol according to claim 1, wherein the viral suspension is diluted in an aqueous solution containing at least 6 to 12 g/l of a salt of a monovalent cation selected from the group consisting of sodium chloride and potassium chloride.

5. The aerosol according to claim 4, wherein the viral suspension is diluted in an aqueous solution containing approximately 9 g/l of a salt of a monovalent cation.

6. A method for delivering an optimum amount of viral particles into the tracheobronchial passages of the respiratory tract of a mammal comprising administering the aerosol of claim 5.

7. A method of increasing the transport of Cl⁻ ions in a lung of a mammal suffering from cystic fibrosis, comprising administering to said mammal in need of increase Cl⁻ transport, a therapeutically effective amount of the viral aerosol of claim 5, wherein said adenoviral particles are replication-defective adenoviral particles encoding a functional CFTR protein, and wherein a sufficient quantity of CFTR protein is produced to increase Cl⁻ secretion in the lung.

8. The aerosol according to claim 1, wherein the viral suspension is diluted in an aqueous solution containing 50 to 100 g/l of a hexose selected from the group consisting of glucose and mannose.

9. The aerosol according to claim 8, wherein the viral suspension is diluted in an aqueous solution containing 50 g/l of glucose.

10. An aerosol according to claim 1, wherein the adenoviral particle is a replication-defective adenoviral particle coding for a functional CFTR protein.

11. A method for delivering an optimum amount of viral particles into the tracheobronchial passages of the respiratory tract of a mammal comprising administering the aerosol of claim 10.

* * * * *